United States Patent

Riebel et al.

[11] 3,950,334
[45] Apr. 13, 1976

[54] O-ALKYL-S-ALKYL-O-[6-ALKYL- OR 6-HALO-PYRIDAZIN-(3)-YL]-(THIONO)THIOL-PHOSPHORIC ACID ESTERS

[75] Inventors: Hans-Jochem Riebel; Lothar Rohe, both of Wuppertal; Ingeborg Hammann, Cologne; Wolfgang Behrenz, Overath-Steinenbrueck, all of Germany

[73] Assignee: Bayer Aktiengesellschaft, Leverkusen, Germany

[22] Filed: Nov. 11, 1974

[21] Appl. No.: 522,404

[30] Foreign Application Priority Data
Nov. 30, 1973 Germany............................ 2359661

[52] U.S. Cl............................ 260/250 AP; 424/200
[51] Int. Cl.²........................................ C07D 237/14
[58] Field of Search.............................. 260/250 AP

[56] References Cited
UNITED STATES PATENTS
2,759,938 8/1956 Du Breuil..................... 260/250 AP
3,878,210 4/1975 Lorenz et al. ................ 260/250 AP Primary Examiner—R. J. Gallagher
Assistant Examiner—Anne Marie T. Tighe
Attorney, Agent, or Firm—Burgess, Dinklage & Sprung

[57] ABSTRACT

O-alkyl-S-alkyl-O[6-alkyl- or 6-halo-pyridazin-(3)-yl]-(thiono)thiolphosphoric acid esters of the formula

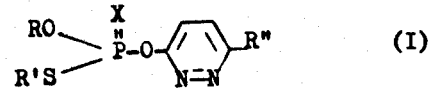

(I)

in which
R and R', which may be identical or different, are each alkyl with 1 to 4 carbon atoms,
R'' is alkyl with 1 to 3 carbon atoms or halogen, and
X is oxygen or sulfur,
which possess insecticidal and acaricidal properties.

4 Claims, No Drawings

O-ALKYL-S-ALKYL-O-[6-ALKYL- OR 6-HALO-PYRIDAZIN-(3)-YL]-(THIONO)THIOLPHOSPHORIC ACID ESTERS

The present invention relates to ahd has for its objects the provision of particular new O-alkyl-S-alkyl-O-[6-alkyl- or 6-halo-pyridazin-(3)-yl]-(thiono)thiolphosphoric acid esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,759,938 and from German Published Specification DOS 1,950,491 that pyridazine-thionophosphoric acid esters, for example, O,O-diethyl-O-[6-chloro-(Compound A) and 6-methyl-pyridazin-(3)-yl]-thionophosphoric acid esters (Compound B), exhibit insecticidal and acaricidal activity. However, these compounds have a high toxicity to warm-blooded animals.

The present invention provides, as new compounds, the pyridazine-(thiono)-thiolphosphoric acid esters of the general formula

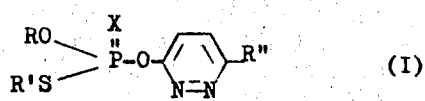   (I)

in which
R and R' each is alkyl with 1 to 4 carbon atoms,
R'' is alkyl with 1 to 3 carbon atoms or halogen, and
X is oxygen or sulfur.

Preferably, R is ethyl or n- or iso-propyl, R' is n-propyl, n-butyl, isobutyl or tert.-butyl, and R'' is methyl, ethyl, chlorine or bromine. Particularly preferred are compounds wherein R is ethyl and R' is n-propyl.

Surprisingly, the pyridazine-(thiono)-thiolphosphoric acid esters of the formula (I) exhibit a better insecticidal and acaricidal action than previously known compounds of analogous structure and of the same type of action, together with a substantially lower toxicity to warm-blooded animals. The compounds can be employed against insects and mites which damage plants, and against pests harmful to health and pests of stored products. The compounds according to the invention thus represent a genuine enrichment of the art.

The present invention also provides a process for the preparation of a pyridazine-(thiono)-thiolphosphoric acid ester of the formula (I), in which a (thiono)-thiolphosphoric acid ester-halide of the general formula

   (II), in which
X, R and R' have the above-mentioned meanings, and Hal is halogen, preferably chlorine,
is reacted with a 3-hydroxypyridazine derivative of the general formula

   (III), in which
R'' has the above-mentioned meaning,
the latter being used as such in the presence of an acid-binding agent or in the form of an alkali metal salt, alkaline earth metal salt or ammonium salt thereof.

If O-ethyl-S-sec.-butyl-thionothiolphosphoric acid ester-chloride and 3-hydroxy-6-bromo-pyridazine are used as starting materials, the course of the reaction can be represented by the following equation:

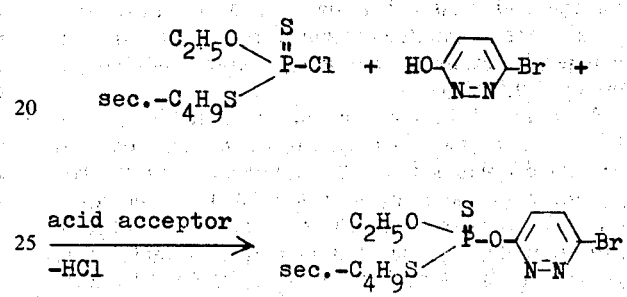

The 3-hydroxypyridazine derivatives of the formula (III) and the (thiono)-thiolphosphoric acid ester-halides (II) which are to be used as starting materials are described in the literature and can be prepared in accordance with known methods, e.g. Helv. Chim. Acta Vol. 37 (1954) page 121, Berichte Vol. 34 (1901) page 3264, USSR Patent Specification 184,863 and published Japanese Patent Application 5536/72.

The following may be mentioned as examples of the (thiono)-thiolphosphoric acid ester-halides and 3-hydroxypyridazine derivatives which can be used: O-ethyl-S-n-pyropyl-, O-ethyl-S-n-butyl-, O-ethyl-S-isobutyl-, O-ethyl-S-tert.-butyl-, O-n-propyl-S-n-propyl-, O-n-propyl-S-n-butyl, O-n-propyl-S-isobutyl-, O-ethyl-S-tert.-butyl, O-isopropyl-S-n-butyl, O-isopropyl-S-isobutyl, and O-isopropyl-S-tert.-butylthiolphosphoric acid ester-chlorides and bromides and the corresponding thiono analogues, and 6-bromo-, 6-chloro-, 6-methyl- or 6--ethyl-3--hydroxypyridazine.

The preparative process is preferably carried out with the use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles such as acetonitrile and propionitrile.

As mentioned above, the reaction may be effected in the presence of an acid-binding agent. All customary acid acceptors can be used for this purpose. Alkali metal carbonates and alkali metal alcoholates, such as sodium carbonate, potassium carbonate, sodium methylate, potassium methylate, sodium ethylate and potassium ethylate, have proved particularly suitable for this purpose, as have aliphatic, aromatic or heterocyclic amines, for example triethylamine, trimethylamine, dimethylaniline, dimethylbenzylamine and pyridine.

The reaction temperatures can be varied within a fairly wide range. In general, the reaction is carried out at between 10° and 100°C, preferably at from 60° to 90°C.

In general, the reaction is allowed to take place under normal pressure.

To carry out the process, the starting materials are in most cases employed in equimolar amounts. An excess of one or other reactant produces no significant advantages. In general, the reaction is carried out in a suitable solvent, preferably in the presence of an acid acceptor, at an elevated temperature. After completion of the reaction, the mixture is cooled, the salts which have separated out are removed and the reaction mixture is treated with an organic solvent, for example toluene, and sodium bicarbonate solution. The organic phase is then separated off and worked up in the usual manner, for example by washing, drying and, if appropriate, distillation.

A number of the new compounds are obtained in the form of oils which in most cases cannot be distilled without decomposition but can be freed from the last volatile constituents by so-called "slight distillation", that is to say by prolonged heating under reduced pressure to moderately elevated temperatures, and can be purified in this way. They are characterized by their refractive indexes.

As already mentioned, the pyridazine-(thiono)-thiolphosphoric acid esters according to the invention are distinguised by an outstanding insecticidal and acaricidal activity coupled with low toxicity to warm-blooded animals. They have a good action against sucking and biting insects.

For this reason, the compounds according to the invention can be employed successfully as pesticides in plant protection and in the hygiene field of protection of stored products.

The pests combatted include sucking and biting insects, diptera and mites.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum* as well as the grape mealybuy (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus and Nephotettix bipunetatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra or Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvets may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc. if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combatting or controlling pests, e.g. insects, and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed, whereas 0% means that none of the spider mites were killed.

The active compounds, the concentrations of the active compounds, the evaluation times and the results can be seen from the following table:

Table 1

| Active compound | (Tetranychus test / resistant) Active compound concentration in % | Degree of destruction in % after 2 days |
|---|---|---|
| (structure: O–P(=S)(OC$_2$H$_5$)$_2$ on pyridine with CH$_3$) (known) (B) | 0.1 0.01 | 100 20 |
| (structure: O–P(=S)(OC$_2$H$_5$)(SC$_3$H$_7$–n) on pyridine with Br) (1) | 0.1 0.01 | 100 100 |

EXAMPLE 2

LT$_{100}$ test for Diptera
Test insects: Musca domestica
Solvent: Acetone 2 parts by weight of active compound were dissoled in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 2

| Active compound | (LT$_{100}$ test for Diptera / Musca domestica) Active compound concentration of the solution in % | LT$_{100}$ in minutes (') or hours (hrs) |
|---|---|---|
| (structure: O–P(=S)(OC$_2$H$_5$)$_2$ on pyridine with CH$_3$) (known) (B) | 0.2 0.02 | 135' 8 hrs |
| (structure: O–P(=S)(OC$_2$H$_5$)(SC$_3$H$_7$–n) on pyridine with Cl) (3) | 0.2 0.02 | 55' 165' |

EXAMPLE 3

Toxicity test/peroral
Test animal: Albino rat (Rattus norvegicus)
Evaluation after: 7 days To produce a suitable preparation of active compound, 3 parts by weight of active compound were mixed with 2.8 parts by weight of highly-dispersible silica and 4.2 parts by weight of talc. Suspensions which contained, in 1 ml of liquid, the amount of active compound to be applied per 100 g of animal weight, were prepared from the above active-compound concentrate, with a little added powdered vegetable gum, by grinding with water. Dosing was effected volumetrically after weighing the test animals. A steel knob-ended probe was used for oral administration. The evaluation was carried out in each case after the end of the above-mentioned time interval, calculated from the administration of the active compound.

The LD$_{50}$ values (dose of active compound at which 50% of the treated animals were killed) were determined in the usual manner from the mortality figures of the doses, which were varied in geometrical progression.

The active compounds and LD$_{50}$ values can be seen from the table which follows:

Table 3

| Active compound | (Toxicity test / Albino rat / peroral) LD$_{50}$ values (in mg/kg of body weight) |
|---|---|
| (structure: O–P(=S)(OC$_2$H$_5$)$_2$ on pyridine with CH$_3$) (known) (B) | 0.5–1 |

Table 3-continued

| Active compound | (Toxicity test / Albino rat / peroral) LD$_{50}$ values (in mg/kg of body weight) |
|---|---|
| ![structure] O-P(OC$_2$H$_5$)$_2$ with S, pyridazine-Cl (known) (A) | approx. 5 |
| ![structure] O-P(=S)(OC$_2$H$_5$)(SC$_3$H$_7$-n), pyridazine-CH$_3$ (2) | approx. 50 |
| ![structure] O-P(=S)(OC$_2$H$_5$)(SC$_3$H$_7$-n), pyridazine-Cl (3) | 100–250 |
| ![structure] O-P(=S)(OC$_2$H$_5$)(SC$_3$H$_7$-n), pyridazine-Br (1) | 100–250 |

The process of the present invention is illustrated in the following preparative Example.

EXAMPLE 4

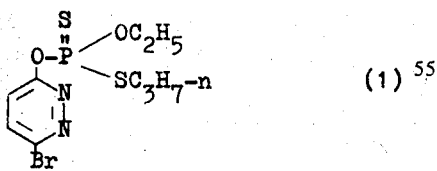

(1)

21.4 g (0.1 mole) of O-ethyl-S-n-propyl-thionothiolphosphoric acid diester-chloride were added dropwise to a mixture of 17.5 g (0.1 mole) of 3-hydroxy-6-bromopyridazine and 14.5 g (0.105 mole) of potassium carbonate in 200 ml of acetonitrile. Thereafter the mixture was warmed to 70°C for 3 hours and was then cooled. The potassium chloride which had precipitated was filtered off. 500 ml of toluene and 200 ml of saturated sodium bicarbonate solution were added to the filtrate. The organic phase was separated off and washed with water, and after drying over sodium sulfate the solvent was removed under reduced pressure and the residue was purified by "slight distillation". 21.5 g (60% of theory) of O-ethyl-S-n-propyl-O-[6-bromo-pyridazin(3)-yl]-thionothiolphosphoric acid ester were obtained in the form of a yellow oil with a refractive index $n_D^{26}$ of 1.5727.

The following compounds were prepared by the same method:

| Compound No. | Formula | Refractive index | Yield (% of theory) |
|---|---|---|---|
| 2 | ![structure] O-P(=S)(OC$_2$H$_5$)(SC$_3$H$_7$-n), pyridazine-CH$_3$ | $n_D^{22}$: 1.5560 | 84 |
| 3 | ![structure] O-P(=S)(OC$_2$H$_5$)(SC$_3$H$_7$-n), pyridazine-Cl | $n_D^{25}$: 1.5770 | 45 |

The following compounds can be prepared similarly:
O-isopropyl-S-tert.-butyl-O-[6-ethyl-pyridazin(3)-yl]-thiolphosphoric acid ester,
O-n-propyl-S-methyl-O-[6-methyl-pyridazin(3)-yl]-thiolphosphoric acid ester,
O-ethyl-S-isobutyl-O-[6-bromo-pyridazin(3)-yl]-thionothiolphosphoric acid ester,
and the like.

It will be appreciated that the instant specification and examples are set forth by way of illustration and not limitation, and that various modifications and changes may be made without departing from the spirit and scope of the present invention.

We claim:
1. An O-ethyl-S-n-propyl -O-(6-substituted-pyridazin(3)-yl)-thiono thiolphosphoric acid ester of the formula

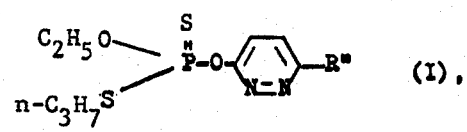

(I), in which
R″ is alkyl with 1 to 3 carbon atoms or halogen.
2. The compound according to claim 1, wherein such compound is O-ethyl-S-n-propyl-O-[6-bromo-pyridazin(3)-yl]-thionothiolphosphoric acid ester of the formula

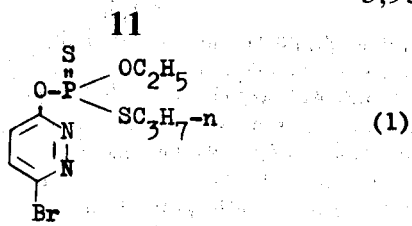
(1)
3. The compound according to claim 1, wherein such compound is O-ethyl-S-n-propyl-O-[6-methyl-pyridazin(3)-yl]-thionothiolphosphoric acid ester of the formula
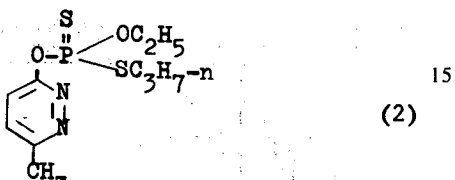
(2)
4. The compound according to claim 1, wherein such compound is O-ethyl-S-n-propyl-O-[6-chloro-pyridazin(3)-yl]-thionothiolphosphoric acid ester of the formula
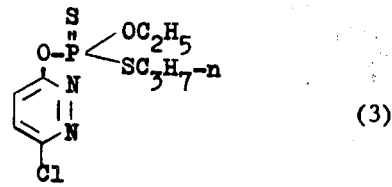
(3)
\* \* \* \* \*